US006423848B2

(12) United States Patent
Bennett

(10) Patent No.: US 6,423,848 B2
(45) Date of Patent: Jul. 23, 2002

(54) TRIDENTATE LIGAND

(75) Inventor: Alison Margaret Anne Bennett, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/729,305

(22) Filed: Dec. 4, 2000

Related U.S. Application Data

(63) Continuation-in-part of application No. 09/273,409, filed on Mar. 22, 1999, which is a continuation-in-part of application No. 08/991,372, filed on Dec. 16, 1997, now Pat. No. 5,955,555
(60) Provisional application No. 60/033,656, filed on Dec. 17, 1996.

(51) Int. Cl.$^7$ ............................................. C07D 211/70
(52) U.S. Cl. ....................................................... 546/329
(58) Field of Search ......................................... 546/329

(56) References Cited

U.S. PATENT DOCUMENTS

| | | | |
|---|---|---|---|
| 5,071,927 A | 12/1991 | Benham et al. |
| 5,137,994 A | 8/1992 | Goode et al. |
| 5,286,589 A | 2/1994 | Go et al. |
| 5,595,705 A | 1/1997 | Walton et al. |
| 5,686,542 A | 11/1997 | Ostoja-Starzewski et al. |
| 5,753,785 A | 5/1998 | Reddy et al. |
| 5,856,610 A | 1/1999 | Tamura et al. |

FOREIGN PATENT DOCUMENTS

| | | |
|---|---|---|
| EP | 0 361 363 | 4/1990 |
| JP | 89-045712 | 10/1989 |
| JP | 02078663 | 3/1990 |
| WO | WO 90/15085 | 12/1990 |
| WO | WO 96 23010 | 8/1996 |
| WO | WO 96/37523 | 11/1996 |
| WO | WO 98/27124 | 6/1998 |
| WO | WO 99/02472 | 1/1999 |
| WO | 9912981 | * 3/1999 |

OTHER PUBLICATIONS

Crisp, CA 130:182102, 1999.*
Bullita, CA 123:111439, 1995.*
Ju, CA 120:79456, 1992.*
Hiratani, CA 114:143077, 1990.*
Karag'ozov, CA 112:98470, 1989.*
Shi, CA 111:153773, 1989.*
Niu, CA 105:226510, 1986.*
Queguiner, CA 72:55178, 1969.*
L. Sacconi, et al., High–spin Five–co–ordinate Nickel(II) and Cobalt(II) Complexes with 2,6–Diacetylpyridinebis(imines), J. Chem. Soc., A, 1510–1515, 1968.
Paul E. Figgins, et al., Complexes of Iron(II), Cobalt(II) and Nickel(II) with Biacetyl–bis–methylimine, 2–Pyidinal–m-ethylimine and 2,6–Pyridindial–bis–methylimine, J. Am. Chem. Soc., 82, 820–824, 1960.
Thomas W. Bell, et al., Molecular Architecture. 1. Sodium, Potassium, and Strontium Complexes of a Hexaazamacrocycle, an 18–Crown–6/Torand Analogue, J. Am. Chem. Soc., 113, 3115–3122, 1991.
Francis Lions, et al., Tridentate Chelate Compounds. I, J. Am. Chem. Soc., 79, 2733–2738, 1957.
Reinhard Nesper, et al., Palladium(II) complexes of chiral tridentate nitrogen pybox ligands, Journal of Organometallic Chemistry, 507, 85–101, 1996.

* cited by examiner

*Primary Examiner*—D. Margaret Seaman

(57) ABSTRACT

Certain 2,6-pyridinecarboxaldehydebis(imine) and 2,6-diacylpyridinebis(imine) compounds are provided, which are particularly suitable for use as tridentate ligands in iron and cobalt olefin polymerization catalysts.

20 Claims, No Drawings

TRIDENTATE LIGAND

CROSS-REFERENCE TO RELATED APPLICATIONS

This application is a continuation-in-part of appplication Ser. No. 09/273,409, filed Mar. 22, 1999, which is a continuation-in-part of application Ser. No. 08/991,372, filed Dec. 16, 1997, now U.S. Pat. No. 5,955,555, which claims the benefit of Provisional Application No. 60/033,656, filed Dec. 17, 1996.

FIELD OF THE INVENTION

Polymers with varied and useful properties may be produced in processes using at least two polymerization catalysts, at least one of which is a selected iron or cobalt catalyst, for the synthesis of polyolefins.

TECHNICAL BACKGROUND

Polyolefins are most often prepared by polymerization processes in which a transition metal containing catalyst system is used. Depending on the process conditions used and the catalyst system chosen, polymers, even those made from the same monomer(s) may have varying properties. Some of the properties which may change are molecular weight and molecular weight distribution, crystallinity, melting point, branching, and glass transition temperature. Except for molecular weight and molecular weight distribution, branching can affect all the other properties mentioned, It is known that certain transition metal containing polymerization catalysts containing iron or cobalt, are especially useful in polymerizing ethylene and propylene, see for instance U.S. patent applications Ser. No. 08/991,372, filed Dec. 16, 1997 (now U.S. Pat. No. 5,955,555), and Ser. No. 09/006,031, filed Jan. 12, 1998 (now U.S. Pat. No. 6,150,482) ("equivalents" of World Patent Applications 98/27124 and 98/30612). It is also known that blends of distinct polymers, that vary for instance in molecular weight, molecular weight distribution, crystallinity, and/or branching, may have advantageous properties compared to "single" polymers. For instance it is known that polymers with broad or bimodal molecular weight distributions may often be melt processed (be shaped) more easily than narrower molecular weight distribution polymers. Also, thermoplastics such as crystalline polymers may often be toughened by blending with elastomeric polymers.

Therefore, methods of producing polymers which inherently produce polymer blends are useful especially if a later separate (and expensive) polymer mixing step can be avoided. However in such polymerizations one should be aware that two different catalysts may interfere with one another, or interact in such a way as to give a single polymer.

Various reports of "simultaneous" oligomerization and polymerization of ethylene to form (in most cases) branched polyethylenes have appeared in the literature, see for instance World Patent Application 90/15085, U.S. Pat. Nos. 5,753,785, 5,856,610, 5,686,542, 5,137,994, and 5,071,927, C. Denger, et al,. Makromol. Chem. Rapid Commun., vol. 12, p. 697–701 (1991), and E. A. Benham, et al., Polymer Engineering and Science, vol. 28, p. 1469–1472 (1988). None of these references specifically describes any of the processes herein or any of the branched homopolyethylenes claimed herein.

SUMMARY OF THE INVENTION

This invention concerns a process for the polymerization of olefins, comprising, contacting under polymerizing conditions:

(a) a first active polymerization catalyst for said olefins which is a Fe or Co complex of a ligand of the formula:

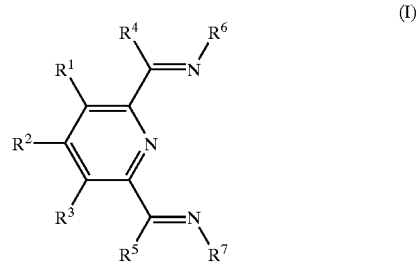

wherein:
$R^1$, $R^2$ and $R^3$ are each independently hydrogen, hydrocarbyl, substituted hydrocarbyl, or an inert functional group;
$R^4$ and $R^5$ are each independently hydrogen, hydrocarbyl, an inert functional group or substituted hydrocarbyl; and
$R^6$ and $R^7$ are aryl or substituted aryl;

(b) a second active polymerization catalyst for said olefins which contains one or more transition metals;

(c) a least one first olefin capable of being polymerized by said first active polymerization catalyst; and (d) at least one second olefin capable of being polymerized by said second active polymerization catalyst.

This invention also concerns a process for the polymerization of olefins, comprising, contacting under polymerizing conditions:

(a) a first active polymerization catalyst for said olefins which is a Fe or Co complex of a ligand of the formula:

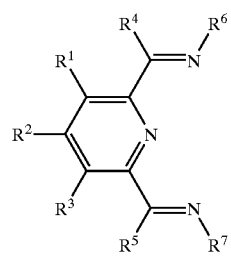

wherein:
$R^1$, $R^2$ and $R^3$ are each independently hydrogen, hydrocarbyl, substituted hydrocarbyl, or an inert functional group;
$R^4$ and $R^5$ are each independently hydrogen, hydrocarbyl, an inert functional group or substituted hydrocarbyl; and
$R^6$ and $R^7$ are aryl or substituted aryl;

(b) a second active polymerization catalyst for said olefins which contains one or more transition metals;

(c) a least one first olefin capable of being polymerized by said first active polymerization catalyst; and (d) at least one second olefin capable of being polymerized by said second active polymerization catalyst;

and provided that:
one or both of said first olefin and said second olefin is ethylene;
one of said first polymerization catalysts and said second polymerization catalyst produces an oligomer of the formula $R^{60}CH{=}CH_2$ from said ethylene, wherein $R^{60}$ is n-alkyl; and a branched polyolefin is a product of said polymerization process.

This invention also concerns a polymerization catalyst component, comprising:

(a) a first active polymerization catalyst for said olefins which is a Fe or Co complex of a ligand of the formula:

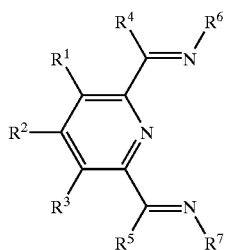

(I)

wherein:
$R^1$, $R^2$ and $R^3$ are each independently hydrogen, hydrocarbyl, substituted hydrocarbyl, or an inert functional group;
$R^4$ and $R^5$ are each independently hydrogen, hydrocarbyl, an inert functional group or substituted hydrocarbyl; and
$R^6$ and $R^7$ are aryl or substituted aryl;

(b) a second active polymerization catalyst for said olefins which contains one or more transition metals;

(c) a catalyst support; and (d) optionally one or more polymerization catalyst activators for one or both of (a) and (b).

Also described herein is a polyolefin containing at least 2 ethyl branches, at least 2 hexyl or longer branches and at least one butyl branch per 1000 methylene groups, and provided that said polyolefin has fewer than 5 methyl branches per 1000 methylene groups.

This invention also includes a polyolefin, containing about 20 to about 150 branches of the formula —$(CH_2CH_2)_n$H wherein n is an integer of 1 to 100, provided that said polyolefin has less than about 20 methyl branches per 1000 methylene groups.

DETAILS OF THE INVENTION

In the polymerization processes and catalyst compositions described herein certain groups may be present. By hydrocarbyl is meant a univalent radical containing only carbon and hydrogen. By substituted hydrocarbyl herein is meant a hydrocarbyl group which contains one or more (types of) substitutents that does not interfere with the operation of the polymerization catalyst system. Suitable substituents in some polymerizations may include some or all of halo, ester, keto (oxo), amino, imino, carboxyl, phosphite, phosphonite, phosphine, phosphinite, thioether, amide, nitrile, and ether. Preferred substituents are halo, ester, amino, imino, carboxyl, phosphite, phosphonite, phosphine, phosphinite, thioether, and amide. Which substitutents are useful in which polymerizations may in some cases be determined by reference to U.S. patent application Ser. No. 08/991,372, filed Dec. 16, 1997 (now U.S. Pat. No. 5,955,555), and Ser. No. 09/006,031, filed Jan. 12, 1998 (now U.S. Pat. No. 6,150,482) (and their corresponding World Patent Applications), both of which are hereby included by reference. By an aryl moiety is meant a univalent group whose free valence is to a carbon atom of an aromatic ring. The aryl moiety may contain one or more aromatic ring and may be substituted by inert groups. By phenyl is meant the $C_6H_5$— radical, and a phenyl moiety or substituted phenyl is a radical in which one or more of the hydrogen atoms is replaced by a substituent group (which may include hydrocarbyl). Preferred substituents for substituted phenyl include those listed above for substituted hydrocarbyl, plus hydrocarbyl. If not otherwise stated, hydrocarbyl, substituted hydrocarbyl and all other groups containing carbon atoms, such as alkyl, preferably contain 1 to 20 carbon atoms.

By a polymerization catalyst activator is meant a compound that reacts with a transition metal compound to form an active polymerization catalyst. A preferred polymerization catalyst activator is an alkylaluminum compound, that is a compound which has one or more alkyl groups bound to an aluminum atom.

By a polymerization catalyst component is meant a composition that by itself, or after reaction with one or more other compounds (optionally in the presence of the olefins to be polymerized), catalyzes the polymerization of olefins.

Noncoordinating ions are mentioned and useful herein. Such anions are well known to the artisan, see for instance W. Beck., et al., Chem. Rev., vol. 88, p. 1405–1421 (1988), and S. H. Strauss, Chem. Rev., vol. 93, p. 927–942 (1993), both of which are hereby included by reference. Relative coordinating abilities of such noncoordinating anions are described in these references, Beck at p. 1411, and Strauss at p. 932, Table III. Useful noncoordinating anions include $SbF_6^-$, BAF, $PF_6^-$, or $BF_4^-$, wherein BAF is tetrakis[3,5-bis(trifluoromethyl)phenyl]borate.

A neutral Lewis acid or a cationic Lewis or Bronsted acid whose counterion is a weakly coordinating anion is also present as part of the catalyst system. By a "neutral Lewis acid" is meant a compound which is a Lewis acid capable of abstracting X from (II) to form a weakly coordination anion.

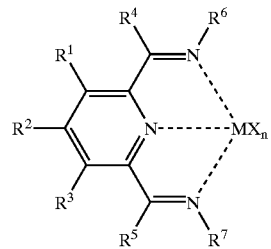

(II)

In (II), M is Co or Fe, each X is independently and anion and each X is such that the total negative charges on X equal the oxidation state of M. The neutral Lewis acid is originally uncharged (i.e., not ionic). Suitable neutral Lewis acids include $SbF_5$, $Ar_3B$ (wherein Ar is aryl), and $BF_3$. By a cationic Lewis acid is meant a cation with a positive charge such as $Ag^+$, $H^+$, and $Na^+$.

In those instances in which (II) does not contain an alkyl or hydride group already bonded to the metal (i.e., X is not alkyl or hydride), the neutral Lewis acid or a cationic Lewis or Bronsted acid also alkylates or adds a hydride to the metal, i.e., causes an alkyl group or hydride to become bonded to the metal atom, or a separate compound is added to add the alkyl or hydride group.

A preferred neutral Lewis acid, which can alkylate the metal, is a selected alkyl aluminum compound, such as $R^9{}_3Al$, $R^9{}_2AlCl$, $R^9AlCl_2$, and "$R^9AlO$" (alkylaluminoxanes), wherein $R^9$ is alkyl containing 1 to 25 carbon atoms, preferably 1 to 4 carbon atoms. Suitable alkyl aluminum compounds include methylaluminoxane (which is an oligomer with the general formula $[MeAlO]_n$), $(C_2H_5)_2AlCl$, $C_2H_5AlCl_2$, and $[(CH_3)_2CHCH_2]_3Al$. Metal hydrides such as $NaBH_4$ may be used to bond hydride groups to the metal M.

For (I) and (II) preferred formulas and compounds are found in U.S. patent applications Ser. No. 08/991,372, filed Dec. 16, 1997 (now U.S. Pat. No. 5,955,555), and Ser. No. 09/006,031, filed Jan. 12, 1998 (now U.S. Pat. No. 6,150,482), and preferred groupings and compounds in these applications are also preferred herein. However the compound numbers and group (i.e., $R^x$) numbers in these applications may vary from those herein, but they are readily convertible. These applications also describe synthesis of (I) and (II).

There are many different ways of preparing active polymerization catalysts from (I) or (II) many of which are described in U.S. patent applications Ser. No. 08/991,372, filed Dec. 16, 1997 (now U.S. Pat. No. 5,955,555), and Ser. No. 09/006,031, filed Jan. 12, 1998 (now U.S. Pat. No. 6150482), and those so described are applicable herein. "Pure" compounds which themselves may be active polymerization catalysts may be used, or the active polymerization catalyst may be prepared in situ by a variety of methods.

For instance, olefins may be polymerized by contacting, at a temperature of about $-100°$ C. to about $+200°$ C. a first compound W, which is a neutral Lewis acid capable of abstracting $X^-$ to form $WX^-$, provided that the anion formed is a weakly coordinating anion; or a cationic Lewis or Bronsted acid whose counterion is a weakly coordinating anion.

Which first active polymerization catalysts will polymerize which olefins, and under what conditions, will also be found in U.S. patent applications Ser. No. 08/991,372, filed Dec. 16, 1997 (now U.S. Pat. No. 5,955,555), and Ser. No. 09/006,031, filed Jan. 12, 1998 (now U.S. Pat. No. 6,150,482). Monomers useful herein for the first active polymerization catalyst include ethylene and propylene. A preferred monomer for this catalyst is ethylene.

In one preferred process described herein the first and second olefins are identical, and preferred olefins in such a process are the same as described immediately above. The first and/or second olefins may also be a single olefin or a mixture of olefins to make a copolymer. Again it is preferred that they be identical, particularly in a process in which polymerization by the first and second polymerization catalysts make polymer simultaneously.

In some processes herein the first active polymerization catalyst may polymerize a monomer that may not be polymerized by said second active polymerization catalyst, and/or vice versa. In that instance two chemically distinct polymers may be produced. In another scenario two monomers would be present, with one polymerization catalyst producing a copolymer, and the other polymerization catalyst producing a homopolymer, or two copolymers may be produced which vary in the molar proportion or repeat units from the various monomers. Other analogous combinations will be evident to the artisan.

In another variation of the process described herein one of the polymerization catalysts makes an oligomer of an olefin, preferably ethylene, which oligomer has the formula $R^{60}CH=CH_2$, wherein $R^{60}$ is n-alkyl, preferably with an even number of carbon atoms. The other polymerization catalyst in the process (co)polymerizes this olefin, either by itself or preferably with at least one other olefin, preferably ethylene, to form a branched polyolefin. Preparation of the oligomer (which is sometimes called an α-olefin) by a first active polymerization-type of catalyst can be found in U.S. patent application Ser. No. 09/005965, filed Jan. 12, 1998 (now U.S. Pat. No. 6,103,946) ("equivalent" of World Patent Application 99/02472), and B. L. Small, et. al., J. Am. Chem. Soc., vol. 120, p. 7143–7144 (1998), all of which are hereby included by reference. These references describe the use of a limited class of compounds such as (II) to prepare compounds of the formula $R^{60}CH=CH_2$ from ethylene, and so would qualify as a catalyst that produces this olefin. In a preferred version of this process one of these first-type polymerization is used to form the α-olefin, and the second active polymerization catalyst is a catalyst which is capable of copolymerizing ethylene and olefins of the formula $R^{60}CH=CH_2$, such as a Ziegler-Natta-type or metallocene-type catalyst. Other types of such catalysts include transition metal complexes of amidimidates and certain iron or cobalt complexes of (I). The amount of branching due to incorporation of the olefin $R^{60}CH=CH_2$ in the polymer can be controlled by the ratio of α-olefin forming polymerization catalyst to higher polymer forming olefin polymerization catalyst. The higher the proportion of α-olefin forming polymerization catalyst the higher the amount of branching. The homopolyethylenes that are made may range from polymers with little branching to polymers which contain many branches, that is from highly crystalline to amorphous homopolyethylenes. In one preferred form, especially when a crystalline polyethylene is being made, the process is carried out in the gas phase. It is believed that in many cases in gas phase polymerization when both catalysts are present in the same particle on which polymerization is taking place (for example originally a supported catalyst), the α-olefin is especially efficiently used (polymerized into the resulting polymer). When amorphous or only slightly crystalline homopolyethylenes are being made the process may be carried out in liquid slurry or solution.

In the variation of the process described in the immediately preceding paragraph a novel homopolyethylene is produced. By "homopolyethylene" in this instance is meant a polymer produced in a polymerization in which ethylene is the only polymerizable olefin added to the polymerization process in a single step, reactor, or by simultaneous reactions. However it is understood that the polymer produced is not made by the direct polymerization of ethylene alone, but by the copolymerization of ethylene and α-olefins which are produced in situ. The polymer produced usually contains only branches of the formula (excluding end groups) —$(CH_2CH_2)_nH$ wherein n is 1 or more, preferably 1 to 100, more preferably 1 to 30, of these branches per 1000 methylene atoms. Normally there will be branches with a range of "n" in the polymer. The amount of these branches (as measured by total methyl groups) in the polymer preferably ranges from about 2 to about 200, especially preferably about 5 to about 175, more preferably about 10 to about 150, and especially preferably about 20 to about 150 branches per 1000 methylene groups in the polymer (for the method of measurement and calculation, see World Patent Application 96/23010). Another preferable range for these branches is about 50 to about 200 methyl groups per 1000 methylene carbon atoms. It is also preferable (either alone or in combination with the other preferable features above) that in these branched polymers there is at least 2 branches each of ethyl and n-hexyl or longer and at least one n-butyl per 1000 methylene groups, more preferably at least 4 branches each of ethyl and n-hexyl or longer and at least 2 n-butyl branches per 1000 methylene groups, and especially preferably at least 10 branches each of ethyl and n-hexyl or longer and at least 5 n-butyl branches per 1000 methylene groups. It is also preferred that there are more ethyl branches than butyl branches in this homopolyethylene. In another preferred polymer (alone or in combination with any of the above preferred features) there is less than 20 methyl branches, more preferably less than 2 methyl branch, and especially preferably less than 2 methyl branches (all after correction for end groups) per 1000 methylene groups.

In the polymerizations to make the "homopolyethylene" only a single high molecular weight polymer is produced, that is a polymer which has an average degree of polymerization of at least 50, more preferably at least 200, and especially preferably at least 400. The synthesis of the branched homopolyethylene is believed to be successful in part because the catalyst which produces the α-olefin often does so at a rate comparable with the polymerization rate, both of them, for the sake of low cost, being relatively rapid.

Likewise, conditions for such polymerizations, particularly for catalysts of the first active polymerization type, will also be found in all of these patent applications. Briefly, the temperature at which the polymerization is carried out is about −100° C. to about +200° C., preferably about −20° C. to about +80° C. The polymerization pressure which is used with a gaseous olefin is not critical, atmospheric pressure to about 275 MPa, or more, being a suitable range. With a liquid monomer the monomer may be used neat or diluted with another liquid (solvent) for the monomer. The ratio of W:(I), when W is present, is preferably about 1 or more, more preferably about 10 or more when only W (no other Lewis acid catalyst) is present. These polymerizations may be batch, semi-batch or continuous processes, and may be carried out in liquid medium or the gas phase (assuming the monomers have the requisite volatility). These details will also be found in U.S. patent applications Ser. No. 08/991,372, filed Dec. 16, 1997 (now U.S. Pat. No. 5,955,555), and Ser. No. 09/006,031, filed Jan. 12, 1998, and Ser. No. 09/005,965, filed Jan. 12, 1998 (now U.S. Pat. No. 6,150,482).

In these polymerization processes preferred groups for $R^6$ is

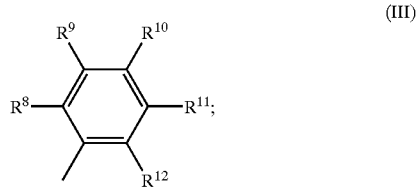

(III)

and for $R^7$ is

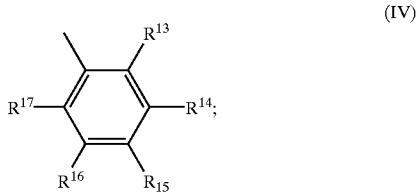

(IV)

wherein:
$R^8$ and $R^{13}$ are each independently hydrocarbyl, substituted hydrocarbyl or an inert functional group;
$R^9$, $R^{10}$, $R^{11}$, $R^{14}$, $R^{15}$ and $R^{16}$ are each independently hydrogen, hydrocarbyl, substituted hydrocarbyl or an inert functional group;
$R^{12}$ and $R^{17}$ are each independently hydrogen, hydrocarbyl, substituted hydrocarbyl or an inert functional group;

and provided that any two of $R^8$, $R^9$, $R^{10}$, $R^{11}$, $R^{12}$, $R^{13}$, $R^{14}$, $R^{15}$, $R^{16}$ and $R^{17}$ that are vicinal to one another, taken together may form a ring.

Two chemically different active polymerization catalysts are used in the polymerization described herein. The first active polymerization catalyst is described in detail above. The second active polymerization catalyst may also meet the limitations of the first active polymerization catalyst, but must be chemically distinct. For instance, it may have a different transition metal present, and/or utilize a ligand which differs in structure between the first and second active polymerization catalysts. In one preferred process, the ligand type and the metal are the same, but the ligands differ in their substituents.

Included within the definition of two active polymerization catalysts are systems in which a single polymerization catalyst is added together with another ligand, preferably the same type of ligand, which can displace the original ligand coordinated to the metal of the original active polymerization catalyst, to produce in situ two different polymerization catalysts.

However other types of catalysts may also be used for the second active polymerization catalyst. For instance so-called Ziegler-Natta and/or metallocene-type catalysts may also be used. These types of catalysts are well known in the polyolefin field, see for instance Angew. Chem., Int. Ed. Engl., vol. 34, p. 1143–1170 (1995), European Patent Application 416,815 and U.S. Pat. No. 5,198,401 for information about metallocene-type catalysts, and J. Boor Jr., Ziegler-Natta Catalysts and Polymerizations, Academic Press, New York, 1979 for information about Ziegler-Natta-type catalysts, all of which are hereby included by reference. Suitable late metal transition catalysts will be found in World Patent Applications 96/23010 and 97/02298, both of which are hereby included by reference. Many of the useful polymerization conditions for these types of catalyst and the first active polymerization catalysts coincide, so conditions for the polymerizations with first and second active polymerization catalysts are easily accessible. Oftentimes the "cocatalyst" or "activator" is needed for metallocene of Ziegler-Natta-type polymerizations, much as W is sometimes needed for polymerizations using the first active polymerization catalysts. In many instances the same compound, such as an alkylaluminum compound, may be used for these purposes for both types of polymerization catalysts.

Suitable catalysts for the second polymerization catalyst also include metallocene-type catalysts, as described in U.S. Pat. No. 5,324,800 and European Patent Application 129,368; particularly advantageous are bridged bis-indenyl metallocenes, for instance as described in U.S. Pat. No. 5,145,819 and European Patent Application 485,823. Another class of suitable catalysts comprises the well-known constrained geometry catalysts, as described in European Patent Applications 416,815, 420,436, 671,404, and 643,066 and World Patent Application 91/04257. Also the class of transition metal complexes described in WO 96/13529 can be used. Also useful are transition metal complexes of bis(carboximidamidatonates), as described in U.S. patent application Ser. No. 08/096,668, filed Sep. 1, 1998.

All the catalysts herein may be "heterogenized" (to form a polymerization catalyst component, for instance) by coating or otherwise attaching them to solid supports, such as silica or alumina. Where an active catalyst species is formed by reaction with a compound such as an alkylaluminum compound, a support on which the alkylaluminum compound is first coated or otherwise attached is contacted with the transition metal compounds (or their precursors) to form a catalyst system in which the active polymerization catalysts are "attached" to the solid support. These supported catalysts may be used in polymerizations in organic liquids. They may also be used in so-called gas phase polymerizations in which the olefin(s) being polymerized are added to the polymerization as gases and no liquid supporting phase is present. The transition metal compounds may also be coated onto a support such as a polyolefin (polyethylene, polypropylene, etc.) support, optionally along with other needed catalyst components such as one or more alkylaluminum compounds.

The molar ratio of the first active polymerization catalyst to the second active polymerization catalyst used will depend on the ratio of polymer from each catalyst desired, and the relative rate of polymerization of each catalyst under the process conditions. For instance, if one wanted to prepare a "toughened" thermoplastic polyethylene that contained 80% crystalline polyethylene and 20% rubbery polyethylene, and the rates of polymerization of the two catalysts were equal, then one would use a 4:1 molar ratio of the catalyst that gave crystalline polyethylene to the catalyst that gave rubbery polyethylene. More than two active polymerization catalysts may also be used if the desired product is to contain more than two different types of polymer.

The polymers made by the first active polymerization catalyst and the second active polymerization catalyst may be made in sequence, i.e., a polymerization with one (either first or second) of the catalysts followed by a polymerization with the other catalyst, as by using two polymerization vessels in series. However it is preferred to carry out the polymerization using the first and second active polymerization catalysts in the same vessel(s), i.e., simultaneously. This is possible because in most instances the first and second active polymerization catalysts are compatible with each other, and they produce their distinctive polymers in the other catalyst's presence.

The polymers produced by this process may vary in molecular weight and/or molecular weight distribution and/or melting point and/or level of crystallinity, and/or glass transition temperature or other factors. For copolymers the polymers may differ in ratios of comonomers if the different polymerization catalysts polymerize the monomers present at different relative rates. The polymers produced are useful as molding and extrusion resins and in films as for packaging. They may have advantages such as improved melt processing, toughness and improved low temperature properties.

In the Examples, all pressures are gauge pressures.

In the Examples the transition metal catalysts were either bought, or if a vendor is not listed, were made. Synthesis of nickel containing catalysts will be found in World Patent Application 96/23010, while synthesis of cobalt and iron containing catalysts will be found in U.S. patent applications Ser. No. 08/991,372, filed Dec. 16, 1997 (now U.S. Pat. No. 5,955,555) and Ser. No. 09/006,031, filed Jan. 12, 1998 (now U.S. Pat. No. 6,150,482).

In the Examples PMAO-IP is a form of methylaluminoxane which stays in solution in toluene, and is commercially available. W440 is a Ziegler-Natta type catalyst of unknown structure available from Akzo Chemicals, Inc., 1 Livingston Ave., Dobbs Ferry, N.Y. 10522, U.S.A.

EXAMPLES 1–9 AND COMPARATIVE EXAMPLES A–E

Ethylene Polymerization General Procedure

The catalyst was weighed into a reaction vessel and was dissolved in about 20 mL of distilled toluene. The reaction was sealed and transferred from the drybox to the hood. The reaction was purged with nitrogen, then ethylene. The PMAO-IP (methylaluminoxane solution) was then quickly added to the vessel and the reaction was put under 35 kPa ethylene. The reaction ran at room temperature in a water bath to help dissipate heat from any exotherm. The ethylene was then turned off and the reaction was quenched with about 15 mL of methanol/HCl solution (90/10 volume %). If polymer was present, the reaction was filtered and the polymer was rinsed with methanol, then acetone and dried overnight in the hood. The resulting polymer was collected and weighed.

Below for each polymerization the catalysts used are listed

Example 1 catalyst 1: 4 mg (0.006 mmol)

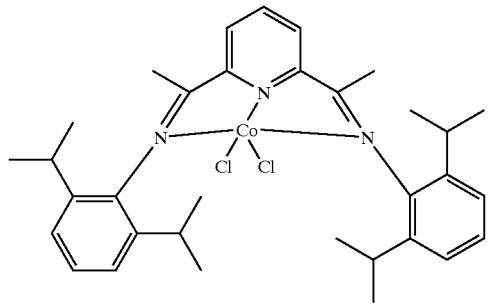

catalyst 2: Zirconocene dichloride, from Stream Chemicals, catalog #93-4002, 2 mg (0.006 mmol)

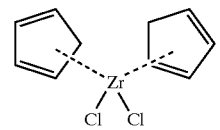

co-catalyst: PMAO-IP; 2.0 mmole Al; 1.0 mL of 2.0M in toluene duration: 4 h polymer: 5.322 g yield Example 2 catalyst 1: 4 mg (0.006 mmol)

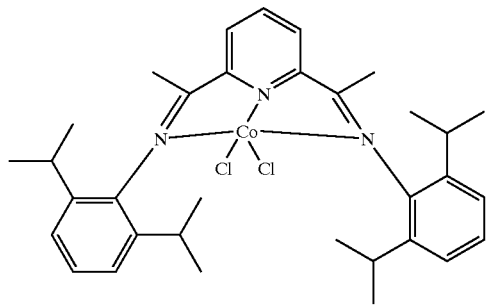

catalyst 2: 4 mg (0.006 mmol)

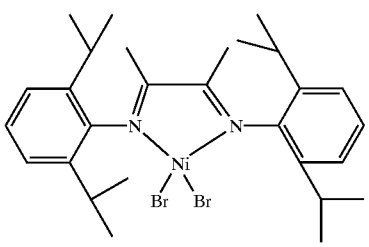

cocatalyst: PMAO-IP; 2.0 mmol Al; 1.0 mL of 2.0M in toluene duration: 4 h polymer: 2.282 g yield Example 3 catalyst 1: 3.5 mg (0.006 mmol)

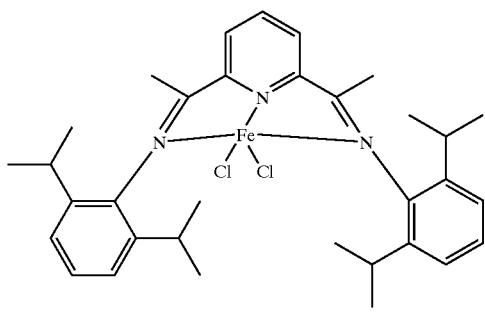

catalyst 2: Zirconocene dichloride, from Strem Chemicals, catalog #53-4002, 2 mg (0.006 mmol)

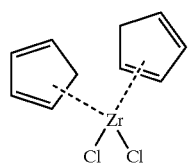

cocatalyst: PMAO-IP; 2.0 mmol Al; 1.0 mL of 2.0M in toluene duration: 4 h polymer: 3.651 g yield Example 4 catalyst 1: 3.5 mg (0.006 mmole)

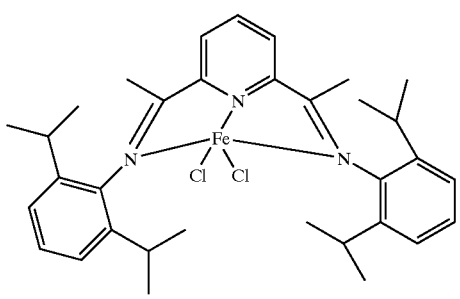

catalyst 2: 4 mg (0.006 mmol)

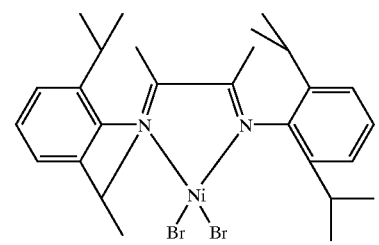

cocatalyst: PMAO-IP; 2.0 mmol Al; 1.0 mL of 2.0M in toluene duration: 4 h polymer: 2.890 g yield Example 5 catalyst 1: 3.5 mg (0.006 mmol)

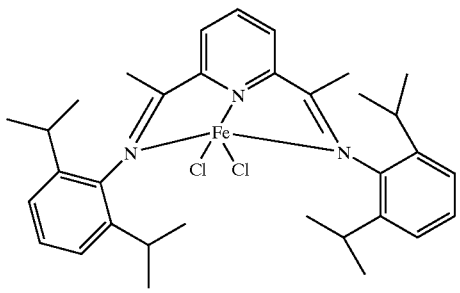

catalyst 2: 4 mg (0.006 mmol)

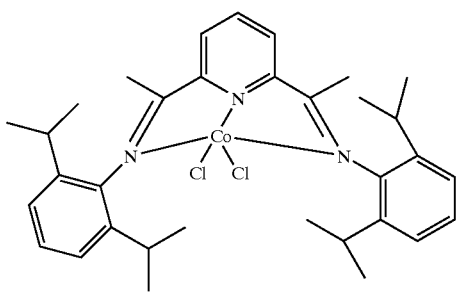

cocatalyst: PMAO-IP; 2.0 mmole Al; 1.0 mL of 2.0M in toluene
duration: 4 h
polymer: 3.926 g yield Example 6 catalyst 1: 4 mg (0.006 mmol)

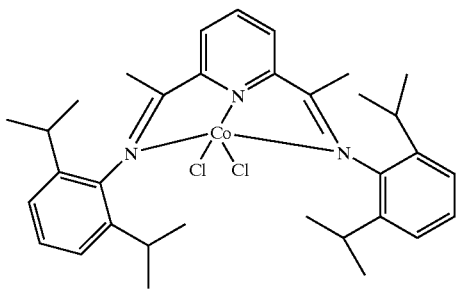

catalyst 2: W440, from Akzo Nobel, 2.3 wt % Ti, 12 mg (0.006 mmole of Ti, based on wt %)
cocatalyst: PMAO-IP; 2.0 mmole Al; 1.0 mL of 2.0M in toluene
duration: 4 h
polymer; 2.643 g yield Example 7 catalyst 1: 3.5 mg (0.006 mmol)

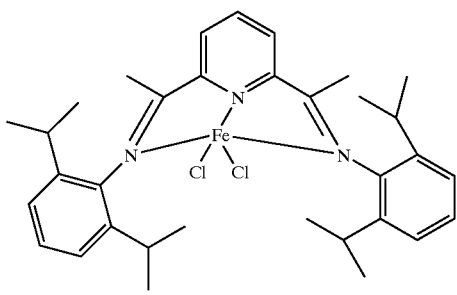

catalyst 2: W440, from Akzo Nobel, 2.3 wt % Ti, 12 mg (0.006 mmole of Ti, based on wt %)
cocatalyst: PMAO-IP; 2.0 mmol Al; 1.0 mL of 2.0M in toluene
duration: 4 h
polymer: 2.943 g yield Example 8 catalyst 1: 4 mg (0.006 mmol)

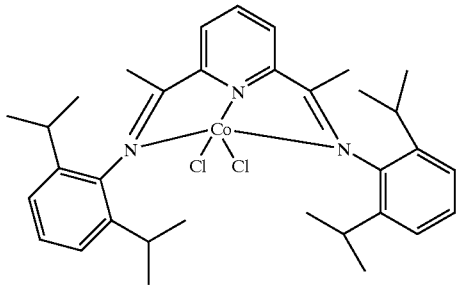

catalyst 2: 4 mg (0.006 mmol)

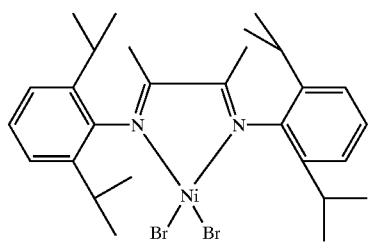

catalyst 3: Zirconocene dichloride, from Strem Chemicals, catalog #93-4002, 2 mg (0.006 mmol)

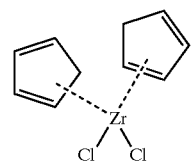

cocatalyst: PMAO-IP; 3.0 mmol Al; 1.5 mL of 2.0M in toluene
duration: 4 h
polymer: 6.178 g yield Example 9 catalyst 1: 3.5 mg (0.006 mmol)

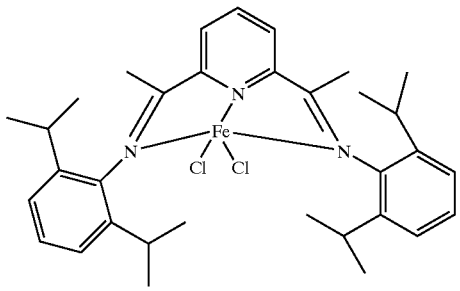

catalyst 2: 4 mg (0.006 mmol)

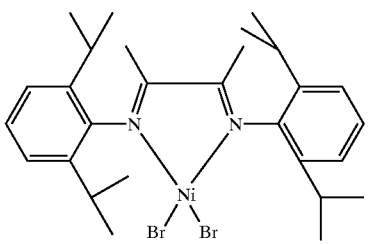

catalyst 3: Zirconocene dichloride, from Strem Chemicals, catalog #93-4002, 2 mg (0.006 mmol)

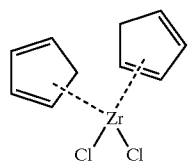

cocatalyst: PMAO-IP; 3.0 mmol Al; 1.5 mL of 2.0M in toluene
duration: 4 h
polymer: 4.408 g yield Comparative Example A catalyst: Zirconocene dichloride, from Strem Chemicals, catalog #93-4002, 2 mg (0.006 mmol)

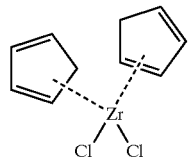

cocatalyst: PMAO-IP; 1.0 mmol Al; 0.5 mL of 2.0M in toluene
duration: 4 h
polymer: 2.936 g yield Comparative Example B catalyst: 4 mg (0.006 mmol)

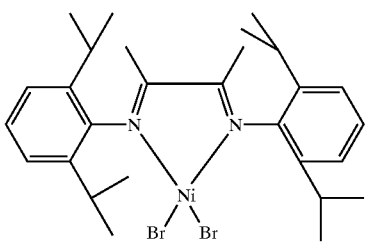

cocatalyst: PMAO-IP; 1.0 mmol Al; 0.5 mL of 2.0M in toluene
duration: 4 h
polymer: 1.053 g yield Comparative Example C catalyst: 4 mg (0.006 mmol)

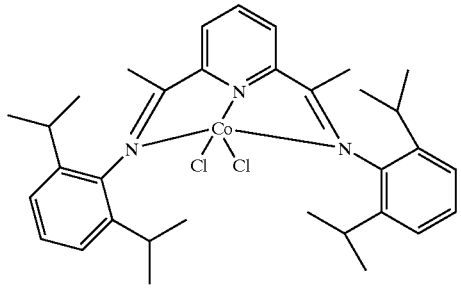

cocatalyst: PMAO-IP; 1.0 mmol Al; 0.5 mL of 2.0M in toluene
duration: 4 h
polymer: 2.614 g yield Comparative Example D catalyst: 3.5 mg (0.006 mmol)

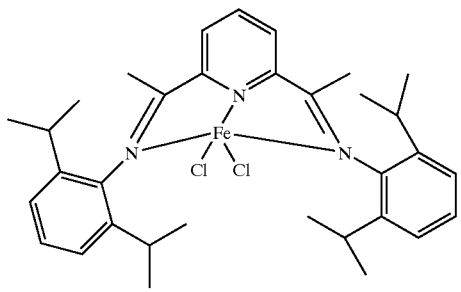

cocatalyst: PMAO-IP; 1.0 mmol Al; 0.5 mL of 2.0M in toluene
duration: 4 h
polymer: 2.231 g yield Comparative Example E catalyst: W440, from Akzo Nobel, 2.3 wt % Ti, 12 mg (0.006 mmole of Ti, based on wt %)
cocatalyst: PMAO-IP; 1.0 mmol Al; 0.5 mL of 2.0M in toluene
duration: 4 h
polymer: 0.326 g yield Examples 10–12

Propylene Polymerization General Procedure

The catalyst was weighed into a reaction vessel and was dissolved in about 20 mL of distilled toluene. The reaction was sealed and transferred from the drybox to the hood. The reaction was purged with nitrogen, then propylene. The MAO was then quickly added to the vessel and the reaction was put under 35 kPa propylene. Reaction ran at 0° C. in an ice bath. The propylene was then turned off and the reaction was quenched with about 15 mL of methanol/HCl solution (90/10 volume %). If polymer was present, the reaction was filtered and the polymer was rinsed with methanol, then acetone and dried overnight in the hood. The resulting polymer was collected and weighed.

Example 10 catalyst 1: 3 mg (0.006 mmol)

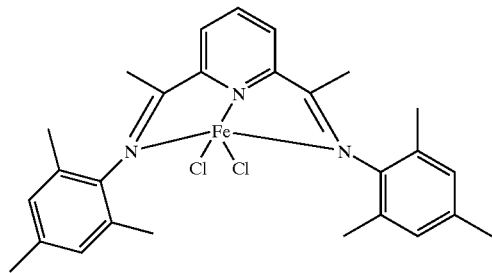

catalyst 2: Zirconocene dichloride, from Strem Chemicals, catalog #93-4002, 2 mg (0.006 mmol)

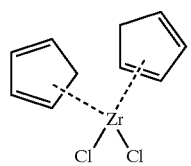

cocatalyst: PMAO-IP; 2.0 mmol Al; 1.0 mL of 2.0M in toluene
duration: 5 h
polymer: 0.471 g yield

Example 11 catalyst 1: 3 mg (0.006 mmol)

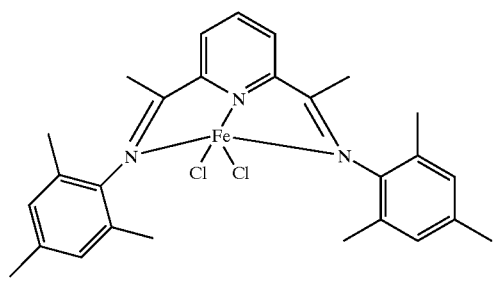

catalyst 2: 4 mg (0.006 mmol)

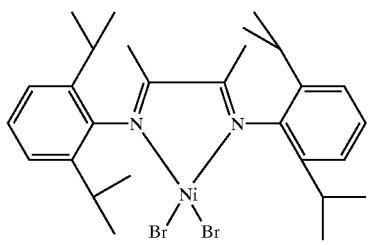

cocatalyst: PMAO-IP; 2.0 mmole Al; 1.0 mL of 2.0M in toluene
duration: 5 h
polymer: 1.191 g yield

Example 12 catalyst 1: 3 mg (0.006 mmol)

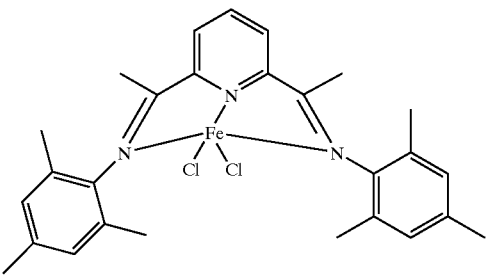

catalyst 2: W440, from Akzo Nobel, 2.3 wt % Ti, 12 mg (0.006 mmole of Ti, based on wt %)
cocatalyst: PMAO-IP; 2.0 mmol Al; 1.0 mL of 2.0M in toluene
duration: 5 h
polymer: 0.238 g yield Examples 13–77 and Comparative Examples F–N In these Examples, compounds A–V and 2 were used as the transition metal compounds.

A

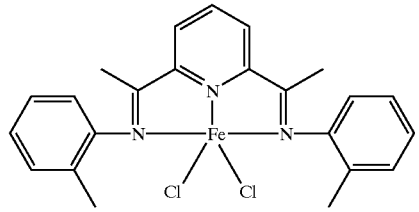

B

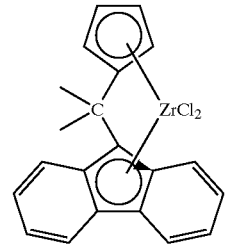

C

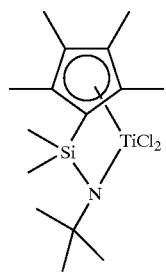

-continued
D
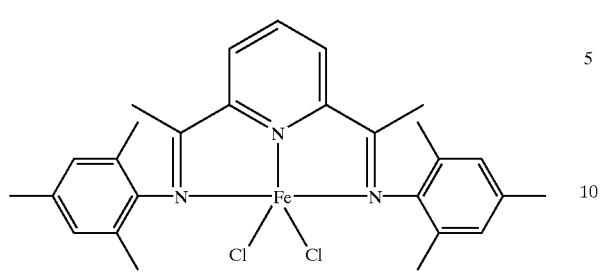
E
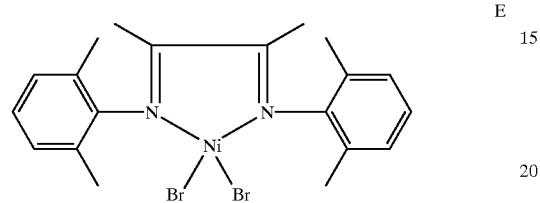
F
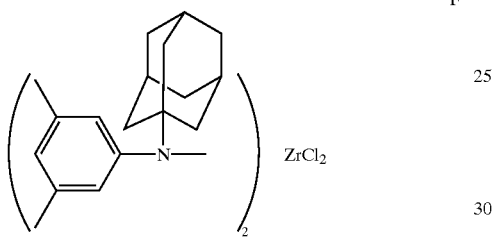
G
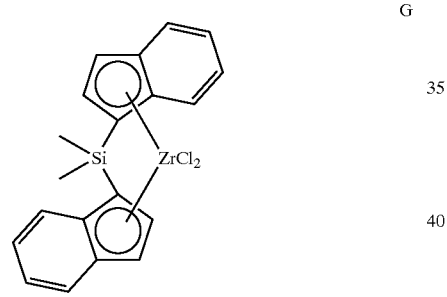
H
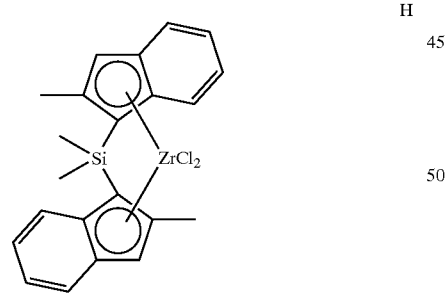
I
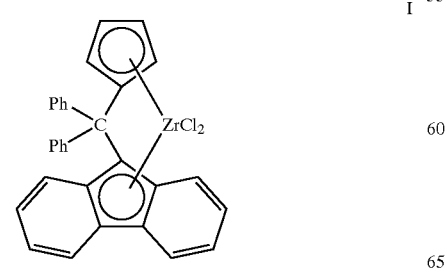
-continued
J
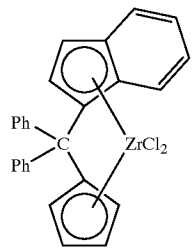
K
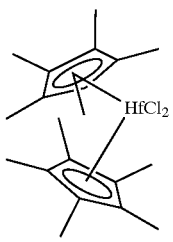
L
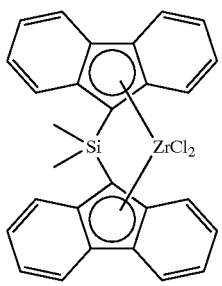
M
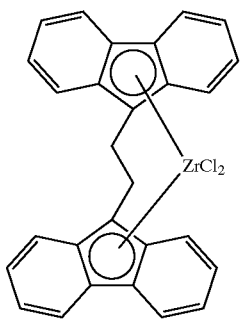
N
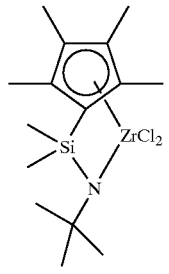

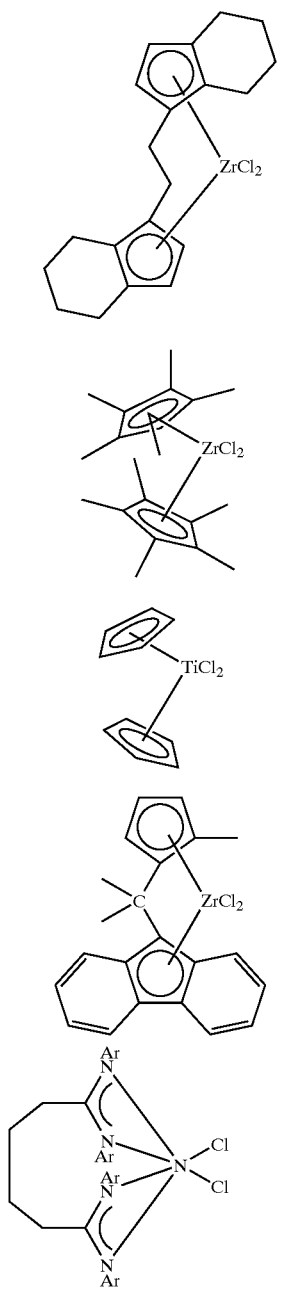

Ar = 2,6-i-Pr—C$_6$H$_4$
S: M = Ti,
T: M = Zr,

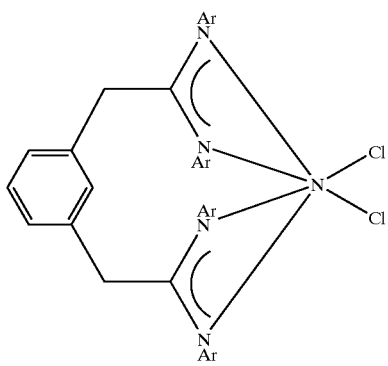

O   Ar = 2,6-i-Pr—C$_6$H$_4$
U: M = Ti,
V: M = Zr,

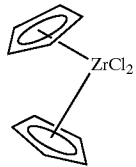

P

Q

R

For preparation of: compound A see B. L. Small, et al., J. Am. Chem. Soc., vol. 120, p. 7143–7144(1998); compound B see Ewen, et al., J. Am. Chem. Soc., vol. 110, p. 6255–6256(1988); compound C see European Patent Application 416,815; compound D World patent Application 98/27124; compound E World patent Application 96/23010; compounds G, H, I and R were purchased from Boulder Scientific company; compounds K, P and 2 were bought from Strem Chemicals Inc.; compound Q was obtained from Aldrich Chemical Co.; compounds S, T, U and V were made by procedures described in U.S. patent application Ser. No. 08/096,668, filed Sep. 1, 1998; compound F was made by reacting ZrCl$_4$ and the amide lithium salt (see J. Chem. Soc., Dalton Trans. 1994, 657) in ether overnight, and removing the ether and pentane extraction gave F 69% yield; compound J was prepared by modifying the procedure of Journal of Organometallic Chemistry 1993, 459, 117–123; compounds L and M were prepared by following the preparation in Macromolecules, 1995, 28, 5399–5404, and Journal of Organometallic Chemistry 1994, 472, 113–118; compound N was made by the procedure described in U.S. Pat. No. 5,096,867; and compound 0 was prepared by following a literature procedure (Ferdinand R. W. P. Wild, et al., Journal of Organometallic Chemistry 1985, 288, 63–67).

EXAMPLES 13–17 AND COMPARATIVE EXAMPLES F–G

A 600 mL Parr® reactor was heated up under vacuum and then allowed to cool under nitrogen. In a drybox, to a Hoke® cylinder was added 5 mL toluene and a certain amount of PMAO-IP (13.5 wt % toluene solution) as shown in Table 1. To a 20 mL vial was added the ethylene (co)polymerization catalyst and 2 mL toluene. The solution was then pipette transferred to a 300 mL RB flask, followed by addition of 150 mL 2,2,4-trimethyl pentane. If catalyst A was used, its toluene suspension was syringe transferred to the flask. The flask was capped with a rubber septa. Both the Hoke® cylinder and the flask were brought out of the drybox. Under nitrogen protection, the transition metal compound solution was cannulated to the reactor. The reactor was pressurized with nitrogen and then the nitrogen was released. The reactor was heated to 70° C., then, pressurized 2× to 690 kPa ethylene, venting each time and finally pressurized to 970 kPa with stirring. The MAO solution was added from the Hoke® cylinder at slightly higher pressure. The ethylene pressure of the reactor wag then adjusted to the desired pressure (Table 1). The reaction mixture was allowed to stir for certain period of time (Table 1). The heating source was removed. Ethylene was vented to about 210 kPa. The reactor was back filled with 1.4 MPa nitrogen and was then vented to 210 kPa. This was repeated once. The reaction mixture was then cooled to RT (room temperature). The reaction mixture was then slowly poured into 400 mL methanol, followed by addition of 6 mL conc. HCl. Upon stirring at RT for 25 min, polymer was filtered, washed with methanol six times and dried in vacuo.

EXAMPLES 18–76 (EXCEPT EXAMPLES 22 AND 23) AND COMPARATIVE EXAMPLES H–N

General procedure for making silica supported catalysts: In a drybox, one of transition metal compounds (but not A), and compound A (0.1 wt % in biphenyl) and silica supported MAO (18 wt % in Al, Albermarle) were mixed with 15 mL of toluene in a 20 mL vial. The vial was shaken for 45 minutes at RT. The solid was filtered, washed with 3×5 mL toluene and dried in vacuo for 1 hour. It was then stored in a freezer in the drybox and was used the same day.

General procedure for gas phase ethylene polymerization by the supported catalysts using a Harper Block Reactor: In a drybox, supported catalysts (5.0 mg or 2.0 mg each, except Example 20 where 15.0 mg was used) were weighed in GC vials. They were placed in a Harper Block Reactor. The reactor was brought out of the drybox and was charged with 1.21 MPa of ethylene. It was then placed in a 90° C. oil bath for 1 h under 1.12 MPa of ethylene. The reactor temperature reached 85° C. after 23 minutes and 87° C. after 35 min. The temperature stayed at 87° C. for the rest of the reaction. (Time, temperature and pressure for Examples in Tables 7–9, as noted.) Ethylene was vented. Polymers were weighed and then submitted for $^1$H NMR analysis (TCE-$d_2$, 120° C.) without purification. Details of these polymerizations are given in Table 2–9.

In Table 10, the branching distribution [in branches per 1,000 methylene ($CH_2$) groups] of the product polymers of selected examples are given. They were determined by $^{13}$C NMR (TCB, 120° C.). Methods for measuring the branching distribution are found in World patent Application 96/23010.

In all the Tables, where provided, branching levels in the polymers, Me/1000$CH_2$ groups, methyl groups per 1000 methylene groups in the polymer, are measured by the method described in World Patent Application 96/23010. In the Tables PE is polyethylene, TON is moles of ethylene polymerized/mole of polymerization catalysts (total of transition metal compounds present)/h, Mn is number average molecular weight, PDI is Mw/Mn where Mw is weight average molecular weight, and P is ethylene pressure. The PMAO-IP used was 13.5 wt. % in toluene. The amount of residual α-olefin in the polymer was estimated by $^1$H NMR, by measurement of the vinylic proton signals of the α-olefin.

TABLE 1

| Ex. No. | Catalyst, amount (× $10^{-6}$ mole) | Catalyst A (× $10^{-6}$ mole) | $P_{C2H4}$ MPa | T (° C.) | Time (min.) | MMAO (mL) | PE yield (g) | # Me Per 1000 $CH_2$ | m. p. (° C.) | Mn/PDI | Density (IR) (g/cm³) |
|---|---|---|---|---|---|---|---|---|---|---|---|
| F  | B, 8.1 | 0    | 1.21 | 70–100  | 35 | 4.2 | 15.0 | 1  | 134      | 43,700/2.2 | 0.952 |
| 13 | B, 8.1 | 0.26 | 1.31 | 81–96   | 25 | 4.2 | 24.0 | 17 | 116, 103 | 32,400/2.2 | 0.914 |
| G  | C, 2.2 | 0    | 1.1  | 90      | 30 | 1.2 | 11.0 | 4  | 132      | 11,700/19.7 | 0.940 |
| 14 | C, 9.5 | 0.06 | 1.31 | 109–126 | 30 | 4.8 | 31.2 | 8  | 133      | 125,000/2.7 | 0.937 |
| 15 | C, 9.5 | 0.13 | 1.34 | 80–120  | 36 | 4.8 | 30.0 | 11 | 119      | 68,400/2.5 | 0.922 |
| 16 | C, 4.6 | 0.26 | 1.3  | 71–96   | 25 | 2.4 | 10.3 | 45 | 121, 56  | 94,000/2.3<br>261/2.8* | 0.895 |
| 17 | C, 3.0 | 2.3  | 1.41 | 100–116 | 43 | 1.5 | 16.6 | 52 | 117, 98<br>84 | 65,000/2.1<br>214/3.4* | 0.922 |

*Bimodal distribution due to α-olefins

TABLE 2

| Ex. No. | Catalyst and amount (× $10^{-6}$ mole) | Catalyst A (× $10^{-6}$ mole) | Al:M:Fe ratio M = Zr, Ti or Fe | PE yield (g) | # Me/1000 $CH_2$ | Tm (° C.) | Mn/PDI | TON |
|---|---|---|---|---|---|---|---|---|
| H  | B, 0.033 | 0      | 1000:1:0    | 0.195 | 5  | 127 | 24,039/5.2  | 210,000 |
| I  | C, 0.033 | 0      | 1000:1:0    | 0.075 | 4  | 126 | 125,451/2.1 | 82,000 |
| 18 | B, 0.033 | 0.001  | 1000:1:0.03 | 0.485 | 15 | 120 | 48,213/4.1  | 500,000 |
| 19 | B, 0.033 | 0.0033 | 1000:1:0.1  | 0.159 | 62 | 125 | 1,916/24.0  | 150,000 |
| 20 | C, 0.099 | 0.0030 | 1000:1:0.03 | 0.200 | 35 | 113 | 63,534/2.7  | 70,000 |
| 21 | D, 0.033 | 0.0017 | 1000:1:0.05 | 0.228 | 4  | 133 | 2,150/26.2  | 240,000 |

TABLE 3

| Ex. No. | Catalyst and amount (× $10^{-6}$ mole) | Catalyst A (× $10^{-6}$ mole) | Al:M:Fe ratio M = Zr, Ti or Fe | PE yield (g) | # Me/1000 $CH_2$ | TON |
|---|---|---|---|---|---|---|
| J | H, 0.033 | 0 | 1000:1:0 | 0.421 | 2 | 460,000 |
| K | I, 0.033 | 0 | 1000:1:0 | 0.135 | 4 | 150,000 |
| L | G, 0.033 | 0 | 1000:1:0 | 0.420 | 2 | 460,000 |
| M | K, 0.033 | 0 | 1000:1:0 | 0.091 | 3 | 99,000 |
| N | R, 0.033 | 0 | 1000:1:0 | 0.203 | 2 | 220,000 |

TABLE 4

| Ex. No. | Catalyst and amount (× 10⁻⁶ mole) | Catalyst A (× 10⁻⁶ mole) | Al:M:Fe ratio M = Zr, Ti or Fe | PE yield (g) | # Me/ 1000 CH$_2$ | Tm (° C.) | Mn/PDI | TON | α-olefins left in polymer |
|---|---|---|---|---|---|---|---|---|---|
| 24 | F, 0.033 | 0.0017 | 1000:1:0.05 | 0.073 | 66 | 120 | 213/18.5 | 76,000 | significant |
| 25 | G, 0.033 | 0.0017 | 1000:1:0.05 | 0.503 | 13 | 122, 115 | 41,525/4.7 | 520,000 | almost none |
| 26 | H, 0.033 | 0.0017 | 1000:1:0.05 | 0.752 | 9 | 120, 115 | 54,825/4.7 | 780,000 | almost none |
| 27 | I, 0.033 | 0.0017 | 1000:1:0.05 | 0.562 | 31 | 119 | 72,982/3.2 | 580,000 | almost none |
| 28 | J, 0.033 | 0.0017 | 1000:1:0.05 | 0.032 | 54 | — | 895/5.6 | 33,000 | small amount |
| 29 | K, 0.033 | 0.0017 | 1000:1:0.05 | 0.240 | 16 | 123 | 1,124/16.5 | 250,000 | small amount |
| 30 | L, 0.033 | 0.0017 | 1000:1:0.05 | 0.112 | 75 | 116, 102 | — | 116,000 | significant |
| 31 | M, 0.033 | 0.0017 | 1000:1:0.05 | 0.092 | 61 | 119 | — | 96,000 | significant |
| 32 | N, 0.033 | 0.0017 | 1000:1:0.05 | 0.068 | 75 | 124 | 485/18.3 | 71,000 | small amount |
| 33 | O, 0.033 | 0.0017 | 1000:1:0.05 | 0.024 | 15 | — | — | 25,000 | almost none |
| 34 | P, 0.033 | 0.0017 | 1000:1:0.05 | 0.019 | 12 | — | — | 20,000 | small amount |
| 35 | Q, 0.033 | 0.0017 | 1000:1:0.05 | 0.082 | 40 | — | — | 85,000 | significant |
| 36 | 2, 0.033 | 0.0017 | 1000:1:0.05 | 0.157 | 7 | — | — | 160,000 | — |
| 37 | R, 0.033 | 0.0017 | 1000:1:0.05 | 0.416 | 10 | 122 | 37,993/7.3 | 450,000 | almost none |
| 38 | S, 0.033 | 0.0017 | 1000:1:0.05 | 0.056 | 59 | — | — | 58,000 | significant |
| 39 | T, 0.033 | 0.0017 | 1000:1:0.05 | 0.023 | 73 | — | — | 24,000 | significant |
| 40 | U, 0.033 | 0.0017 | 1000:1:0.05 | 0.102 | 69 | — | — | 110,000 | significant |
| 41 | V, 0.033 | 0.0017 | 1000:1:0.05 | 0.059 | 78 | — | — | 61,000 | significant |

TABLE 5*

| Ex. No. | Catalyst and amount (× 10⁻⁶ mole) | Catalyst A (× 10⁻⁶ mole) | Al:M:Fe ratio M = Zr, Ti or Fe | yield (g) | # Me/ 1000 CH$_2$ | Mn/PDI | TON | α-olefins left in polymer |
|---|---|---|---|---|---|---|---|---|
| 42 | D, 0.033 | 0.0033 | 1000:1:0.10 | 0.481 | 8 | 3,346/48.6 | 360,000 | significant |
| 43 | D, 0.033 | 0.0082 | 1000:1:0.25 | 0.534 | 14 | 402/156.0 | 350,000 | significant |
| 44 | D, 0.033 | 0.016 | 1000:1:0.50 | 0.566 | 20 | 800/103.0 | 310,000 | significant |

*Reaction time here is 80 minutes

TABLE 6

| Ex. No. | Catalyst and amount (× 10⁻⁶ mole) | Catalyst A (× 10⁻⁶ mole) | Al:M:Fe ratio M = Zr, Ti or Fe | PE yield (g) | # Me/ 1000 CH$_2$ | Tm (° C.) | Mn/PDI | TON | Density (g/cm³) |
|---|---|---|---|---|---|---|---|---|---|
| 45 | H, 0.033 | 0.0017 | 1000:1:0.05 | 0.772 | 6 | 124 | 43,791/6.0 | 800,000 | 0.930 |
| 46 | H, 0.013 | 0.0007 | 1000:1:0.05 | 0.367 | 8 | 124 | 82,151/3.7 | 950,000 | — |
| 47 | I, 0.033 | 0.0017 | 1000:1:0.05 | 0.566 | 38 | 114 | 70,462/4.0 | 590,000 | 0.909 |
| 48 | I, 0.013 | 0.0007 | 1000:1:0.05 | 0.226 | 32 | — | — | 590,000 | — |
| 49 | B, 0.033 | 0.0010 | 1000:1:0.03 | 0.442 | 8 | 127 | 52,673/4.9 | 460,000 | 0.928 |
| 50 | B, 0.033 | 0.0010 | 1000:1:0.03 | 0.563 | 17 | 120 | 52,350/4.9 | 600,000 | — |
| 51 | B, 0.013 | 0.0004 | 1000:1:0.03 | 0.134 | 16 | — | — | 350,000 | — |
| 52 | H, 0.033 | 0.0010 | 1000:1:0.03 | 0.699 | — | — | — | 740,000 | — |
| 53 | N, 0.013 | 0.0004 | 1000:1:0.03 | 0.362 | 6 | 124 | 55,102/5.0 | 960,000 | — |
| 54 | I, 0.033 | 0.0010 | 1000:1:0.03 | 0.376 | 15 | 118 | 98,599/4.0 | 400,000 | — |
| 55 | G, 0.033 | 0.0010 | 1000:1:0.03 | 0.665 | 5 | 124 | 38,693/6.0 | 700,000 | — |

TABLE 7*

| Ex. No. | Catalyst and amount (× 10⁻⁶ mole) | Catalyst A (× 10⁻⁶ mole) | Al:M:Fe ratio M = Zr, Ti or Fe | PE yield (g) | # Me/ 1000 CH$_2$ | Tm (° C.) | Mn/PDI | TON |
|---|---|---|---|---|---|---|---|---|
| 56 | B, 0.033 | 0.0017 | 1000:1:0.05 | 0.740 | 22 | 118, 101 | 54,573/4.0 | 380,000 |
| 57 | B, 0.013 | 0.0007 | 1000:1:0.05 | 0.206 | 24 | — | — | 270,000 |
| 58 | H, 0.033 | 0.0017 | 1000:1:0.05 | 1.158 | 7 | 121 | 92,063/4.9 | 600,000 |
| 59 | H, 0.013 | 0.0007 | 1000:1:0.05 | 0.651 | 12 | — | — | 850,000 |
| 60 | I, 0.033 | 0.0017 | 1000:1:0.05 | 0.439 | 24 | 102 | 102,798/3.8 | 230,000 |
| 61 | I, 0.013 | 0.0007 | 1000:1:0.05 | 0.390 | 25 | — | — | 510,000 |
| 62 | G, 0.033 | 0.0017 | 1000:1:0.05 | 0.871 | 9 | 121 | 45,311/4.7 | 450,000 |

*Two h at 70° C. and 2.4 MPa ethylene pressure.

TABLE 8*

| Ex. No. | Catalyst and amount (× 10⁻⁶ mole) | Catalyst A (× 10⁻⁶ mole) | Al:M:Fe ratio M = Zr, Ti or Fe | PE yield (g) | TON |
|---|---|---|---|---|---|
| 63 | B, 0.013 | 0.0007 | 1000:1:0.05 | 0.143 | 370,000 |
| 64 | B, 0.013 | 0.0007 | 1000:1:0.05 | 0.115 | 300,000 |
| 65 | H, 0.013 | 0.0007 | 1000:1:0.05 | 0.305 | 790,000 |
| 66 | H, 0.013 | 0.0007 | 1000:1:0.05 | 0.215 | 560,000 |
| 67 | I, 0.013 | 0.0007 | 1000:1:0.05 | 0.093 | 240,000 |
| 68 | I, 0.013 | 0.0007 | 1000:1:0.05 | 0.108 | 280,000 |
| 69 | G, 0.013 | 0.0007 | 1000:1:0.05 | 0.349 | 900,000 |

One h at 90° C. at 2.4 MPa ethylene pressure.

TABLE 9*

| Ex. No. | Catalyst and amount (× 10⁻⁶ mole) | Catalyst A (× 10⁻⁶ mole) | Al:M:Fe ratio M = Zr, Ti or Fe | PE yield (g) | # Me/1000 CH$_2$ | Mn/PDI | TON |
|---|---|---|---|---|---|---|---|
| 70 | B, 0.033 | 0.0017 | 1000:1:0.05 | 0.534 | 37 | 42,448/3.4 | 280,000 |
| 71 | B, 0.033 | 0.0017 | 1000:1:0.05 | 0.489 | 45 | — | 250,000 |
| 72 | H, 0.033 | 0.0017 | 1000:1:0.05 | 0.969 | 17 | 77,142/4.8 | 500,000 |
| 73 | H, 0.033 | 0.0017 | 1000:1:0.05 | 1.027 | 11 | — | 530,000 |
| 74 | I, 0.033 | 0.0017 | 1000:1:0.05 | 0.442 | 34 | 96,383/4.2 | 230,000 |
| 75 | I, 0.033 | 0.0017 | 1000:1:0.05 | 0.466 | 32 | — | 240,000 |
| 76 | G, 0.033 | 0.0017 | 1000:1:0.05 | 0.710 | 8 | 39,693/4.9 | 370,000 |

*Two h at 60° C., 2.4 MPa ethylene pressure

TABLE 10

| Ex. No. | Total Me | Me | Et | Pr | Bu | Am | Hex and higher |
|---|---|---|---|---|---|---|---|
| 15 | 10.5 | 0 | 4.6 | 0 | 2.4 | 0 | 4.3 |
| 13 | 16 | 0 | 6.5 | 0 | 3.2 | 0 | 6.5 |
| 26 | 6.9 | 0 | 2.9 | 0 | 0.4 | 0 | 2.5 |
| 47 | 23 | 0 | 8.6 | 0 | 4.7 | 0 | 10.7 |
| 49 | 8.1 | 0 | 3.6 | 0 | 1.3 | 0 | 3.1 |

Example 22

In a drybox, 1.7 mg Compound E and 1.0 mg Compound A were mixed with 40 mL toluene in a Schlenk flask. This was brought out of the drybox and was purged with ethylene for 15 min at 0° C. MAO toluene solution (0.64 mL 13.5 wt %) was injected. The mixture was allowed to stir under 0 kPa ethylene at 0° C. for 12 min. Methanol (100 mL) was injected, followed by 1 mL conc. HCl. Upon stirring for 25 min at RT, the white solid was filtered, washed with 6×20 mL methanol and dried in vacuo. White solid (2.9 g) was obtained. $^1$HNMR in TCE-d$_2$ at 120° C.: 44Me/1000CH$_2$. The polymer contained a significant amount of α-olefins.

Example 23

In a drybox, 30.5 mg of Compound A was mixed with 30.5 g biphenyl in a 100 mL Pyrex® glass bottle. This was stirred in a 100° C. bath for 25 minutes, during which time Compound A dissolved in biphenyl to form a deep green solution. The solution was allowed to cool down to become solid. A 0.1 wt % Compound A/biphenyl homogeneous mixture was obtained.

Example 77

A 600 mL Parr® reactor was heated up under vacuum and then allowed to cool under nitrogen. In a drybox, to a 300 mL RB flask was added 150 mL 2,2,4-trimethylpentane. The flask was capped with a rubber septum. The flask was brought out of the drybox. Under nitrogen protection, the 2,2,4-trimethylpentane solvent was cannulated into the reactor. The reactor was pressured up with nitrogen and then nitrogen was released. This was repeated one more time. The reactor was heated to 70° C. Then in a drybox, 160 mg supported catalyst(made by following the general procedure of preparing silica supported catalysts, it contained 0.0011 mmole of compound B, 0.000057 mmole compound A and 1.1 mmole of MAO) was mixed with 4 mL cyclohexane and was transferred to a 5 mL gas tight syringe with long needle. This was brought out of the drybox and was injected into the reactor under nitrogen protection (positive nitrogen pressure). The reactor was pressured up with 1.2 MPa of nitrogen, then released to 14 kPa. This was repeated one more time. Under stirring, the reactor was pressured up with ethylene to 1.2 MPa. The reaction mixture was allowed to stir at between 70° C. to 97° C. for 60 min. Heating source was removed. Ethylene was vented to about 210 kPa. The reactor was back filled with 1.4 MPa nitrogen and was released to 140 kPa. This was repeated twice. The solution was poured into 300 mL methanol. The polymer was filtered, washed with 6×50 mL methanol and dried in vacuo. White polymer (19.7 g) was obtained. $^1$HNMR in TCE-d$_2$ at 120° C.: 34Me/1000CH$_2$. Mw=98,991; Mn=35,416(PDI= 2.8). Density: 0.902 g/cm$^3$. Melt Index: 1.03(190° C.). $^{13}$CNMR(120° C., TCE-d$_2$): Total Me was 29.4(Me=0; Et=10.8; Pr=0.0; Bu=6.0; Hex and higher=11.7).

What is claimed is:
1. A compound of the formula

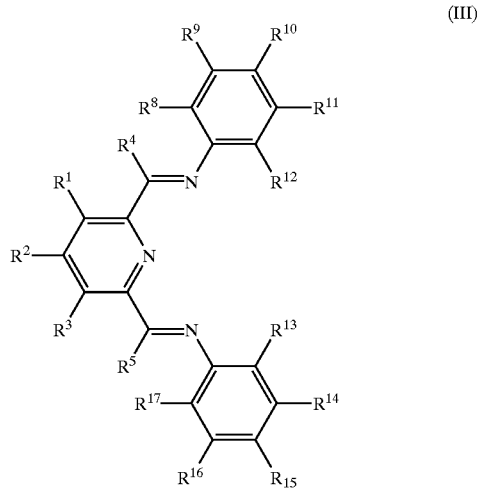

(III)

wherein:

R$^1$, R$^2$ and R$^3$ are each independently hydrogen, hydrocarbyl, substituted hydrocarbyl, or an inert functional group;

R$^4$ and R$^5$ are each independently hydrogen, hydrocarbyl or substituted hydrocarbyl;

R$^8$, R$^{12}$, R$^{13}$ and R$^{17}$ are each independently hydrocarbyl, substituted hydrocarbyl or an inert functional group;

R$^9$, R$^{10}$, R$^{11}$, R$^{14}$, R$^{15}$ and R$^{16}$ are each independently hydrogen, hydrocarbyl, substituted hydrocarbyl or an inert functional group;

and provided that any two of R$^8$, R$^9$, R$^{10}$, R$^{11}$, R$^{12}$, R$^{13}$, R$^{14}$, R$^{15}$, R$^{16}$ and R$^{17}$ that are vicinal to one another taken together may form a ring.

2. The compound as recited in claim 1 wherein;

R$^1$, R$^2$ and R$^3$ are hydrogen;

R$^9$, R$^{10}$, R$^{11}$, R$^{14}$, R$^{15}$ and R$^{16}$ are each independently halogen, halogen alkyl containing 1 to 6 carbon atoms, or hydrogen;

R$^8$, R$^{12}$, R$^{13}$ and R$^{17}$ is each independently halogen, phenyl or alkyl containing 1 to 6 carbon atoms; and R$^4$ and R$^5$ are each independently hydrogen or alkyl containing 1 to 6 carbon atoms.

3. The compound as recited in claim 2 wherein R$^{10}$, R$^{11}$, R$^{12}$, R$^{14}$, R$^{15}$ and R$^{16}$ are each hydrogen.

4. The compound as recited in claim 2 wherein R$^8$, R$^{12}$, R$^{13}$, and R$^{17}$ are each alkyl containing 1–6 carbon atoms.

5. The compound as recited in claim 3 wherein R$^8$, R$^{12}$, R$^{13}$, and R$^{17}$ are each alkyl containing 1–6 carbon atoms.

6. The compound as recited in claim 2 wherein R$^4$ and R$^5$ are each hydrogen or methyl.

7. The compound as recited in claim 2 wherein R$^1$, R$^2$, R$^3$, R$^9$, R$^{11}$, R$^{14}$ and R$^{16}$ are hydrogen, and R$^4$, R$^5$, R$^8$, R$^{10}$, R$^{12}$, R$^{13}$, R$^{15}$ and R$^{17}$ are methyl.

8. The compound as recited in claim 2 wherein R$^1$, R$^2$, R$^3$, R$^9$, R$^{10}$, R$^{11}$, R$^{14}$, R$^{15}$ and R$^{16}$ are hydrogen, R$^4$ and R$^5$ are methylthio, and R$^8$, R$^{12}$, R$^{13}$ and R$^{17}$ are i-propyl.

9. The compound as recited in claim 2 wherein R$^1$, R$^2$, R$^3$, R$^9$, R$^{10}$, R$^{11}$, R$^{14}$, R$^{15}$ and R$^{16}$ are hydrogen, R$^4$ and R$^5$ are 1-imidazolyl, and R$^8$, R$^{12}$, R$^{13}$ and R$^{17}$ are i-propyl.

10. The compound as recited in claim 2 wherein R$^1$, R$^2$, R$^3$, R$^9$, R$^{10}$, R$^{11}$, R$^{14}$, R$^{15}$ and R$^{16}$ are hydrogen, R$^8$ and R$^{13}$ are chloro, and R$^4$, R$^5$, R$^{12}$ and R$^{17}$ are methyl.

11. The compound as recited in claim 2 wherein R$^1$, R$^2$, R$^3$, R$^9$, R$^{10}$, R$^{11}$, R$^{14}$, R$^{15}$ and R$^{16}$ are hydrogen, R$^4$ and R$^5$ are methyl, and R$^8$, R$^{12}$, R$^{13}$ and R$^{17}$ are i-propyl.

12. The compound as recited in claim 2 wherein R$^8$, R$^{12}$, R$^{13}$ and R$^{17}$ are each phenyl.

13. The compound as recited in claim 3 wherein R$^8$, R$^{12}$, R$^{13}$ and R$^{17}$ are each phenyl.

14. The compound as recited in claim 6 wherein R$^8$, R$^{12}$, R$^{13}$ and R$^{17}$ are each phenyl.

15. The compound as recited in claim 1 wherein R$^8$, R$^{12}$, R$^{13}$ and R$^{17}$ are each independently halogen, phenyl or alkyl containing 1 to 6 carbon atoms.

16. The compound as recited in claim 15 wherein R$^8$, R$^{12}$, R$^{13}$ and R$^{17}$ are each phenyl.

17. The compound as recited in claim 15 wherein:

R$^1$, R$^2$ and R$^3$ are hydrogen; and

R$^4$ and R$^5$ are each independently hydrogen or alkyl containing 1 to 6 carbon atoms.

18. The compound as recited in claim 16 wherein:

R$^1$, R$^2$ and R$^3$ are hydrogen; and

R$^4$ and R$^5$ are each independently hydrogen or alkyl containing 1 to 6 carbon atoms.

19. The compound as recited in claim 1 wherein:

R$^9$, R$^{11}$, R$^{14}$ and R$^{16}$ are each hydrogen; and

R$^8$, R$^{10}$, R$^{12}$, R$^{13}$, R$^{15}$ and R$^{17}$ is each independently an alkyl containing 1 to 6 carbon atoms.

20. The compound as recited in claim 19 wherein:

R$^1$, R$^2$ and R$^3$ are hydrogen; and

R$^4$ and R$^5$ are each independently hydrogen or alkyl containing 1 to 6 carbon atoms.

\* \* \* \* \*